US005777155A

United States Patent [19]
Sato et al.

[11] Patent Number: 5,777,155
[45] Date of Patent: Jul. 7, 1998

[54] PROCESS FOR PRODUCING UNSATURATED GLYCOL DIESTER

[75] Inventors: Masato Sato, Kanagawa; Hironobu Ohno, Tokyo; Nobuyuki Murai; Hiroshi Iwasaka, both of Mie, all of Japan

[73] Assignee: Mitsubishi Chemical Corporation, Tokyo, Japan

[21] Appl. No.: 819,199

[22] Filed: Mar. 17, 1997

Related U.S. Application Data

[63] Continuation of Ser. No. 321,039, Oct. 6, 1994, abandoned.

[30] Foreign Application Priority Data

Oct. 6, 1993 [JP] Japan ............... 5-272961

[51] Int. Cl.⁶ ............... C07C 67/05; C07C 67/04
[52] U.S. Cl. ............... 560/244; 560/246
[58] Field of Search ............... 560/244, 246

[56] References Cited

U.S. PATENT DOCUMENTS

| | | | |
|---|---|---|---|
| 3,755,423 | 8/1973 | Onoda et al. | 560/244 |
| 3,922,300 | 11/1975 | Onoda et al. | 560/244 |
| 4,074,413 | 2/1978 | Tanabe | 560/244 |
| 4,075,413 | 2/1978 | Tanabe | 560/244 |
| 4,225,727 | 9/1980 | Kamiyama et al. | 560/244 |
| 5,177,254 | 1/1993 | Haji et al. | 560/244 |

FOREIGN PATENT DOCUMENTS

| | | | |
|---|---|---|---|
| 0036715 | 9/1981 | European Pat. Off. | |
| 0289725 | 11/1988 | European Pat. Off. | C07C 69/16 |
| 4911812 | 2/1974 | Japan . | |
| 5315491 | 5/1978 | Japan | C07C 69/16 |
| 5951850 | 12/1984 | Japan | B01J 27/02 |
| 63277643 | 3/1989 | Japan | C07C 67/04 |

*Primary Examiner*—Gary Geist
*Assistant Examiner*—Rosalynd Keys
*Attorney, Agent, or Firm*—Sughrue, Mion, Zinn, Macpeak & Seas, PLLC

[57] ABSTRACT

A process for producing an unsaturated glycol diester disclosed, which process comprises reacting a conjugated diene with a carboxylic acid and molecular oxygen in the presence of a solid catalyst comprising (1) palladium and (2) tellurium as active components supported on a carrier, wherein a said carrier is a solid carrier in which a proportion of the volume of pores having a pore radius in the range of from 5 to 50 nm is 80% or more relative to the total volume of pores having a pore radius in the range of from 1.8 to 10,000 nm.

18 Claims, No Drawings

PROCESS FOR PRODUCING UNSATURATED GLYCOL DIESTER

This is a Continuation of application Ser. No. 08/321,039 filed Oct. 6, 1994, now abandoned.

FIELD OF THE INVENTION

This invention relates to a process for producing an unsaturated glycol diester which comprises reacting a conjugated diene with a carboxylic acid and molecular oxygen in the presence of a solid catalyst comprising (1) palladium and (2) tellurium supported on a carrier.

BACKGROUND OF THE INVENTION

Unsaturated glycol diesters, for example, 1,4-butenediol diesters, are important intermediate compounds for 1,4-butanediol which is a raw material for engineering plastics, and tetrahydrofuran. Tetrahydrofuran per se is a solvent having a high performance, and a polymer thereof, i.e., polytetramethylene ether glycol is one of the important raw materials for elastic fibers.

Hitherto, various processes for producing the butenediol diester have been proposed, and, of these conventional processes, a process comprising reacting butadiene with a carboxylic acid and molecular oxygen in the presence of a solid catalyst wherein tellurium and palladium are supported on active carbon to produce the butenediol diester is well known in the art.

More specifically, these conventional processes include, for example, a process using a solid catalyst containing palladium and at least one of tellurium and selenium, as disclosed in JP-A-48-72090 (the term "JP-A" as used herein means an "unexamined published Japanese patent application"), a process using a solid catalyst containing palladium, at least one of antimony and bismuth, and at least one of tellurium and selenium, as disclosed in JP-A-48-96513, a process using, as a carrier for the solid catalyst used in the above-described processes, an active carbon which has been pretreated with nitric acid for the purpose of improving the catalytic activity of the solid catalyst, as disclosed in JP-A-49-11812, and a process using a specific solid catalyst prepared by subjecting the solid catalyst used in the above-described processes to a reduction treatment, treating the resulting catalyst with a gas containing molecular oxygen at a temperature of 200° C. or more, and further subjecting the catalyst to a reduction treatment, as disclosed in JP-B-52-12686 (the term "JP-B" as used herein means an "examined published Japanese patent application").

Although the catalysts used in these conventional processes generally show high catalytic activities and selectivities, improvements on the problems of these catalysts, such as elution of the supported metals from the catalyst and lowering of the catalytic activity with the lapse of time, have been desired.

In order to prevent the lowering of the catalytic activity with the lapse of time, some improved processes have been proposed, for example, a process in which the reaction is conducted in the presence of a polymerization inhibitor while limiting the amount of impurities such as vinylcyclohexene in butadiene or formic acid in acetic acid, as disclosed in JP-B-53-15491, and a process in which the reaction is conducted in the presence of elementary sulfur as a deterioration inhibitor, as disclosed in JP-A-52-51313. These processes improve the above-described defects of the solid catalyst to a certain extent, but the improvements are considered still unsatisfactory.

For solving the above-described conventional problems, the present inventors extensively studied with respect to effects of catalyst carriers on the catalytic performance, and, as a result, completed the present invention.

SUMMARY OF THE INVENTION

That is, an object of the present invention is to provide a process for producing an unsaturated glycol diester advantageously on an industrial scale by reacting a conjugated diene with a carboxylic acid and molecular oxygen in the presence of a solid catalyst having a high activity and a very low degree of decrease of activity (deactivation) with the lapse of time.

The above object of the present invention can be achieved by the process for producing an unsaturated glycol diester which comprises reacting a conjugated diene with a carboxylic acid and molecular oxygen in the presence of a solid catalyst using, as a carrier for the catalyst, a solid carrier in which a proportion of the volume of pores having a pore radius in the range of from 5 to 50 nm is 80% or more relative to the total volume of pores having a pore radius in the range of from 1.8 to 10,000 nm.

DETAILED DESCRIPTION OF THE INVENTION

The catalyst used in the present invention comprises (1) palladium and (2) tellurium as catalyst components supported on the solid carrier having the above-described specific pore distribution. The pore volume in the present invention is measured by using a mercury porosimeter, that is, the pore volume determined under the condition of $\phi=480$ dyne/cm and $\theta=140°$ in the following basic formula (1) regarding the relationship between the pore radius and the pressure in the method for measurement of the pore:

$$Pr = -2\phi \cos \theta \qquad (1)$$

wherein P represents a pressure, r represents a pore radius, $\phi$ represents a surface tension of mercury, and $\theta$ represents a contact angle between mercury and a sample. More specifically, the catalyst used in the present invention comprises palladium and tellurium as catalyst components supported on a solid carrier in which a proportion of pore volume having a pore radius in the range of from 5 to 50 nm is 80% or more, preferably 85% or more, and more preferably 90% or more, relative to the total pore volume having a pore radius in the range of from 1.8 nm to 10,000 nm, as determined by the above method.

In the present invention, the ratio of palladium and tellurium, which is another component of the catalyst, contained in a catalyst is in the range of from 0.05 to 5 gram atom, preferably from 0.15 to 4 gram atom, and more preferably from 0.15 to 0.5 gram atom of tellurium per gram atom of palladium.

A plant used for producing an unsaturated glycol diester by reacting a conjugated diene with a carboxylic acid and molecular oxygen is generally operated continuously for a period of about a half year to one year and hence it is strongly desirable that the catalytic activity does not decrease during the operating period. It is considered that, for the catalyst having a low degree of deactivation, it is necessary that palladium and tellurium as catalyst components are highly dispersed in the form of metals or alloys thereof on the carrier and that these metals are not coated with high boiling point substances produced as by-products for a long period of time. Generally, an average particle diameter of palladium and tellurium in the catalyst used for the production of unsaturated glycol diesters is considered several ten angstrom (several nm).

In the present invention, good performance of the carrier having a specific pore distribution used in the present invention is considered for the following reasons. That is, in macropores having a pore diameter of more than 100 nm, the density of the active catalyst components supported on the surface of macropores tends to be small due to a low specific surface area whereby the activity of the catalyst is low. On the other hand, in micropores having a pore diameter of less than 10 nm, the micropores may easily be blocked by high boiling point substances produced by the reaction as by-products, for example, polymers of the conjugated diene whereby the catalytic activity of the catalyst metals supported on the surface of such micropores tends to decrease at a relatively high rate with the lapse of time.

Thus, according to the present invention, a catalyst having a high and long-lasting activity can be obtained by supporting the catalyst metals on the solid carrier in which most of the pores have a pore radius in the range of from 5 to 50 nm (10 to 100 nm in diameter).

In the present invention, a carrier may be used having small amount of pore volume, but generally a carrier having a pore volume of 0.8 cc/g or more is advantageously used since a large amount of palladium and tellurium can be supported on such a carrier.

Further, the specific surface area of the solid carrier used in the present invention is not specifically limited as long as the solid carrier satisfies the above-described requirements of the pore volume. However, the solid carrier having a specific surface area of less than 200 m$^2$/g is preferred, particularly one of specific surface area of from 30 to 190 m$^2$/g is preferred. The carrier having a big specific surface area of more than 200 m$^2$/g is not preferred because of the presence of too much micropores.

The shape of the solid carrier used in the present invention is not particularly limited, and any of a powder form, a crushed form, a particle form, a cylindrical form or the like can be used. However, from the industrial standpoint, a carrier having a longest diameter of from about 2.0 mm to about 6.0 mm and a packed density of 0.35 g/ml or more is preferably used. As such a solid carrier, silica, alumina, titania, zeolite, silica-alumia, etc. which has been molded into a predetermined shape can be used. As the solid carrier which satisfies the above-described requirements and is made of silica, a commercialy available silica, such as S980G (tradename, produced by Shell Chemical Co., Ltd.), CARIACT15 (tradename produced by Fuji Devison Co., Ltd.) and so on can be preferably used. In addition, active carbon can also be used as long as it safisfies the above-described requirements.

In supporting the catalytically active metal components on a solid carrier, a conventional method for preparing a carrier-supported metal catalyst can be appropriately used. For example, a typical method comprises dissolving a palladium compound and a tellurium compound in an aqueous solution of nitric acid, immersing a solid carrier into the resulting solution thereby supporting the above metal components on the carrier by impregnation or absorption, separating the carrier having the supported catalyst components by filtration, drying it in air or an appropriate drying gas, and finally reducing it in a gas stream of hydrogen or a reductive organic compound.

The palladium compounds which can be used in the present invention include palladium nitrate, palladium chloride, palladium aetate, and a palladium ammine complex, and, if desired, palladium metal can be used. The concentration of palladium in the catalyst is generally in the range of from 0.5 to 10% by weight and, preferably, from 2 to 6% by weight. When the concentration is less than 0.5% by weight, preparation of a catalyst having a high activity is difficult, and, when the concentration is more than 10% by weight, it is impossible to prepare a catalyst having a preferred proportion of tellurium. More specifically, in order to maintain a preferred proportion of tellurium and palladium (atomic ratio of tellurium/palladium) in the catalyst, it is necessary to increase a concentration of tellurium to a certain degree in the solution used for impregnation in proportion to the concentration of palladium in the solution. However, since the solubility of tellurium (or a tellurium compound) in the solution is generally low as compared with the solubility of palladium (or a palladium compound), and, thus, at a concentration of palladium higher than the above-described upper limit (10% by weight), it is difficult to ensure a preferred proportion of tellurium and palladium.

Examples of tellurium compounds which can be used for the preparation of the catalyst include a halide such as tellurium(II) chloride and tellurium(IV) chloride, an oxide such as tellurium(IV) oxide and tellurium(VI) oxide, telluric acid ($H_6TeO_6$), and tellurium metal.

The amount of tellurium supported on the carrier is generally selected from the range of from 0.05 to 5 gram atom, preferbly from 0.15 to 4 gram atom, and more preferably from 0.15 to 0.5 gram atom, per gram atom of the supported palladium in the catalyst. When the catalyst having a proportion of tellurium below the lower limit of above atomic ratio is used for the reaction according to the present invention, palladium tends to be eluted from the catalyst to the reacton solution during the reaction, and, when the proportion of tellurium in the catalyst exceeds the above-described upper limit, tellurium tends to be eluted from the catalyst during the reaction. In either case, such an elution of one of the metal components of the catalyst causes the lowering of the catalytic activity, and the catalyst does not endure the continuous use for a long period of time.

In supporting the catalyst components on the solid carrier by impregnation or absorption using an aqueous solution of the palladium compound and the tellurium compound, a ratio of the total volume of the aqueous solution and the total pore volume of the carrier, i.e., a volume ratio of (total volume of the aqueous solution used)/(total pore volume of the carrier used), is preferably 0.8 or more, and, more preferably, the volume ratio is selected in the range of from 0.9 to 1.1. When the above volume ratio is below 0.8, palladium and tellurium cannot be supported uniformly. On the other hand, when the above volume ratio exceeds 1.1, an excess amount of the solution which remains unabsorbed must be recovered.

The solid carrier impregnated with the palladium compound and the tellurium compound is then dried. The drying can be achieved by forming a fixed bed with the impregnated solid carrier, and passing a heated nitrogen, air, or hydrogen gas through the bed. In this case, the volume of gas flow is selected from a space velocity (SV) of 20 (1/1·hour) or more, and preferably in the range of from 1,000 to 8,000 (1/1·hour). When the SV value is too low, the drying time becomes too long, and, when the SV value is too high, the volume of the drying gas used becomes too large, with the cost of the drying step being expensive.

The moisture content in the gas used for drying is generally 2% by weight or less, but the moisture content not more than 0.5% by weight is preferred. When the moisture content in the drying gas is too high, the activity of the catalyst finally obtained decreases. The drying temperature is generally selected in the range of from about 40° to about 150° C., but, it is preferred that the catalyst is previously dried by passing a drying gas having a temperature of from about 60° to about 100° C., and then a drying gas having a temperature of from about 140° to about 150° C. is passed to complete the drying process.

The activation treatment of the dried catalyst can be achieved by either of a process comprising alternately repeating a reduction treatment with a reducing gas such as hydrogen and an oxidation treatment with a mixed gas of oxygen and nitrogen, or a process comprising a single reduction treatment with a reducing gas.

The conjugated diene, for example, butadiene, used as a starting material for producing the unsaturated glycol diester using the above-described catalyst is not necessarily a pure diene and may contain an inert gas such as a nitrogen gas, a saturated hydrocarbon such as methane, ethane and butane, or a unsaturated hydrocarbon such as butene. Examples of other conjugated dienes which can be used include isoprene and an alkyl-substituted butadiene such as 2,3-dimethylbutadiene and piperylene.

Another starting material, a carboxylic acid, can be an aliphatic carboxylic acid, preferably a lower ($C_2$–$C_6$) aliphatic monocarboxylic acid, for example, acetic acid, propionic acid and butyric acid. From the standpoint of the reactivity and the cost, acetic acid is particularly preferred. Generally, the carboxylic acid also serves as a reaction medium, but an organic solvent which is inert to the reaction, for example, a saturated hydrocarbon or an ester may be used together as a reaction medium. In this case, however, it is preferred that 50% by weight or more of the reaction medium is the carboxylic acid starting material. The amount of the carboxylic acid starting material used is preferably in the range of from a stoichiometric amount to 60 mols per mol of the conjugated diene.

The molecular oxygen used in the process of the present invention is not necessarily pure oxygen, and oxygen diluted with an inert gas such as nitrogen, for example, air, may be used. The amount of oxygen to be used is not limited, and can be in any amount as long as the gas in the reaction system does not become an explosive composition.

The reaction of molecular oxygen, the conjugated diene and the carboxylic acid in the presence of the solid catalyst according to the present invention can be carried out in a batch manner or a continuous manner, and the catalyst can be used in any system such as a fixed bed, a fluidized bed, a suspended tank system, etc.

The reaction is generally carried out at a temperature of 20° C. or more, preferably from about 20° to about 150° C., but, considering the reaction rate and the formation of by-products, a reaction temperature in the range of from about 50° to about 120° C. is preferred. With consideration of the reaction rate and the cost of reaction equipment, a reaction pressure in the range of from about 5 to about 100 kg/cm$^2$ is preferred.

The present invention is further illustrated by the following examples, but these examples are not to be construed as limiting the present invention.

In the following examples and comparative examples, with respect to the carrier for the catalyst, a ratio of the volume of pores having a pore radius in the range of from 5 to 50 nm to the total volume of pores having a pore radius in the range of from 1.8 to 10,000 nm, that is, [(volume of pores having a pore radius in the range of from 5 to 50 nm)/(total volume of pores having a pore radius in the range of from 1.8 to 10,000 nm)×100] is referred to as "A ratio (%)".

EXAMPLE 1

57 g of an aqueous solution containing 10% by weight of palladium nitrate calculated as palladium metal and 140 g of an aqueous solution prepared by dissolving 2.6 g of tellurium dioxide in 35% nitric acid were added to 56 g of a silica carrier having a particle diameter of 2.4 to 3.4 mm and an A ratio of 97% (S980G produced by Shell Chemical Co., Ltd.; pore volume, 1.12 cc/g; average pore radius, 22.6 nm; specific surface area, 67 m$^2$/g), and, after maintained at 30° C. for 2 hours, the resulting mixture was allowed to cool for 5 hours. Then, the mixture was filtered to recover the silica carrier, and a liquid fraction was removed from the carrier by centrifugation to obtain 136 g of a catalyst.

The resulting catalyst was placed in a pyrex glass tube having an inside diameter of 4.6 cm (an effective cross-sectional area, 16.6 cm$^2$) and maintained at 65° C. for 6 hours and then at an elevated temperature of 100° C. for 2 hours to dry the catalyst. Then, after elevating the temperature to 150° C., the temperature was elevated at a rate of 50° C. per hour while passing a hydrogen gas at a flow rate of 330 Nl/hour. After maintained at 300° C. for 4 hours, the catalyst was cooled in a nitrogen gas stream to obtain 60 g of an activated catalyst. The resulting catalyst contained 4.9% by weight of palladium and 1.8% by weight of tellurium.

Then, 4 g of the catalyst was charged into a stainless steel reaction tube having an inside diameter of 12 mm (an effective cross-sectional area, 1.005 cm$^2$), and the reaction was carried out continuously for 3,900 hours at a reaction pressure of 60 kg/cm$^2$ and a reaction temperature of 80° C. while supplying 1,3-butadiene and acetic acid in a liquid phase at a rate of 0.122 mol/hour and 2.5 mol/hour, respectively, and a nitrogen gas containing 6% by volume of oxygen in a gas phase at a rate of 96.4 Nl/hour.

After starting the reaction, a reaction solution was periodically analyzed at predetermined periods of time to determine the production amount of diacetoxybutene per 1 g of the catalyst per hour, and a constant (k) of the reaction rate was calculated, and a deactivation ratio of the catalytic activity was determined. The results obtained are shown in Table 1 below.

EXAMPLE 2

Diacetoxybutene was produced in the same manner as described in Example 1 except for using, as a carrier for the catalyst, a silica carrier produced by Fuji Devison Co., Ltd. having an A ratio of 99% (trade name, CARIACT15; particle diameter, 2.4 to 4.0 mm; pore volume, 0.91 cc/g; average pore radius, 10.3 nm; specific surface area, 170 m$^2$/g). The results obtained are shown in Table 1 below.

COMPARATIVE EXAMPLE 1

Diacetoxybutene was produced in the same manner as described in Example 1 except for using, as a carrier for the catalyst, a silica carrier produced by Fuji Devison Co., Ltd. having an A ratio of 67% (trade name, CARIACT10; particle diameter, 2.4 to 4.0 mm; pore volume, 0.94 cc/g; average pore radius, 5.8 nm; specific surface area, 273 m$^2$/g). The results obtained are shown in Table 1 below.

COMPARATIVE EXAMPLE 2

60 g of water and 60 g of a 60 wt. % aqueous solution of nitric acid were added to 40 g of a molded peat carbon having an A ratio of 29% (trade name, Sorbonorit-2X, a product of Norit Co., Ltd. (Netherlands); cylindrical form having a diameter of 2 mm and a length of 6 mm; pore volume, 0.69 cc/g, average pore radius, 460 nm; specific surface area, 1058 m²/g) as a carrier for catalyst, and the mixture was maintained at 90 ° to 94° C. for 3 hours. After cooling, the mixture was filtered to remove the solution to obtained active carbon which had been treated with nitric acid.

Then, 20 g of an aqueous solution containing 10% by weight of palladium nitrate calculated as palladium metal and 120 g of an aqueous solution prepared by dissolving 0.55 g of tellurium metal in 35% nitric acid were added to the above-described active carbon, and, after maintained for 3 hours at 30° C., the mixture was allowed to cool for 5 hours. After removing the solution by filtration, the solid material was dried under a reduced pressure of 240 torr at a maximum temperature of 140° C. for 8 hours to obtain a palladium and tellurium supported active carbon containing 4.2% by weight of palladium and 0.78% by weight of tellurium (hereinafter referred to as a supported catalyst).

30 cc of the above-described supported catalyst was charged into a pyrex glass tube having an inside diameter of 2.5 cm (an effective cross-secional area, 4.9 cm²), and the temperature was elevated to 350° C. at a rate of 50° C. per hour while passing nitrogen containing 8% by volume of methanol at a flow rate of 39 Nl/hour. After maintained at that temperature for 4 hours, the supported catalyst was allowed to cool to room temperature in a nitrogen gas stream.

Then, the temperature of the supported catalyst was elevated to 300° C. while passing a nitrogen gas containing 2% by volume of oxygen at a flow rate of 39 Nl/hour, and, after maintained at that temperature for 10 hours, the catalyst was allowed to cool to room temperature in a nitrogen gas stream.

Then, the temperature of the catalyst was elevated to 350° C. at a rate of 50° C. per hour while passing a nitrogen gas containing 8% by volume of methanol at a flow rate of 39 Nl/hour, and, after maintained at that temperature for 15 hours, the catalyst was allowed to cool to room temperature in a nitrogen gas stream.

Then, the temperature was elevated to 300° C. while passing a nitrogen gas containing 2% by volume of oxygen at a flow rate of 39 Nl/hour, and, after maintained at that temperature for 4 hours, the catalyst was allowed to cool to room temperature in a nitrogen gas stream.

Then, the temperature was elevated to 350° C. at a rate of 50° C. per hour while passing a hydrogen gas at a flow rate of 39 Nl/hour, and, after maintained at that temperature for 4 hours, the catalyst was allowed to cool to room temperature in a nitrogen gas stream.

Then, the temperature was elevated to 300° C. while passing nitrogen containing 2% by volume of oxygen at a flow rate of 39 Nl/hour, and, after maintained at that temperature for 15 hours, the catalyst was allowed to cool to room temperature in a nitrogen gas stream.

Then, the temperature was elevated to 350° C. at a rate of 50° C. per hour while passing a hydrogen gas at a flow rate of 39 Nl/hour, and, after maintained at that temperature for 4 hours, the catalyst was allowed to cool to room temperature in a nitrogen gas stream.

The supported catalyst prepared by the activation treatment comprising the repeated oxidation and reduction as described above was found to contain 4.7% by weight of palladium and 0.87% by weight of tellurium.

Thereafter, 4 g of the resulting catalyst was charged into a stainless steel reaction tube having an inside diameter of 12 mm (an effective cross-sectional area of 0.848 cm²), and the reaction was conducted continuously at a reaction pressure of 60 kg/cm², and at a reaction temperature of 80° C. for 3,800 hours, while supplying 1,3-butadiene and acetic acid in a liquid phase at a rate of 0.122 mol/hour and 2.5 mol/hour, respectively, and nitrogen containing 6% by volume of oxygen in a gas phase at a rate of 96.4 Nl/hour.

After starting the reaction, a reaction solution was periodically analyzed at predetermined periods of time to determine the production amount of diacetoxybutene per 1 g of the catalyst per hour, and a constant (k) of the reaction rate was calculated, and a deactivation ratio of the catalytic activity was determined. The results obtained are shown in Table 1 below.

COMPARATIVE EXMPLE 3

Diacetoxybutene was produced in the same manner as described in Comparative Example 2 except for using a crushed active carbon made from coconut shell having an A ratio of 24% (size, 4 to 6 mesh; pore volume, 0.35 cc/g; average pore radius, 180 nm; specific surface area, 1020 m²/g) as a catalyst carrier. The results obtained are shown in Table 1.

TABLE 1

|  | Example 1 | Example 2 | Comparative Example 1 | Comparative Example 2 | Comparative Example 3 |
|---|---|---|---|---|---|
| A Ratio (%) of Carrier Pore | 97 | 99 | 67 | 29 | 24 |
| Carrier Pore Volume (cc/g) | 1.12 | 0.91 | 0.94 | 0.69 | 0.35 |
| Carrier Average Pore Radius (nm) | 22.6 | 8.8 | 5.8 | 460 | 180 |
| Carrier Specific Surface Area (m²/g) | 67 | 170 | 273 | 1058 | 1020 |
| Catalyst Pd Concentration (% by weight) | 4.9 | 4.7 | 4.5 | 4.7 | 3.4 |
| Catalyst Te/Pd Atomic Ratio | 0.30 | 0.16 | 0.17 | 0.16 | 0.19 |
| Reaction Time (t) (hour) | 3900 | 8600 | 700 | 3800 | 4400 |
| Initial Activity ($k_0$) | 6.5 | 7.5 | 7.3 | 6.3 | 4.4 |
| Activity After t Hours (k) | 5.8 | 6.4 | 2.4 | 3.4 | 1.4 |
| Deactivation (%) | 11 | 15 | 67 | 46 | 68 |
| Deactivation Rate | 0.042 | 0.050 | 0.36 | 0.18 | 0.26 |

The reaction time (t) shows the time (hour) after starting the reaction, and the constant of the reaction rate at that time is indicated as "k".

The initial activity indicates the constant of the reaction rate after 10 hours starting the reaction, and is referred to as "$k_0$".

The deactivation (%) is a value calculated by the formula:

$$|(k_0-k)/k_0|\times 100$$

The deactivation rate is a value calculated by the formula:

$$[(1-(k/k_0)]/\log(t/10)$$

The specific surface area (m²/g) is a value determined from the adsorbing amount of nitrogen at a liquid nitrogen temperature by the BET method.

The pore volume (cc/g) is the total volume of pores having a pore radius in the range of from 1.8 nm to 10,000 nm, with the pore radius being measured by using a mercury porosimeter.

The average pore radius (nm) is a value evaluated based on the pore volume. The average pore radius is a pore radius at which accumulated pore volume reaches at half the total volume of pores having a pore radius in the range of from 1.8 to 10,000 nm.

EXAMPLE 3

After the reaction was conducted in the same manner as described in Example 2 for 8,600 hours, the catalyst was taken out of the reaction tube, washed with toluene for 8 hours by means of Soxhlet's extractor and dried under reduced pressure for 6 hours by means of vacuum desiccator set at 150° C.

The weight (w) of the resulting catalyst was measured and the deposition rate of high boiling point substances (% by weight) was calculated according to the following formula:

The Deposition Rate of High Boiling Point Substances=[(w/w$_0$)-1]×100 (% by weight)

wherein, w$_0$ represents the weight of catalyst before reaction. Then, the specific surface area (m$^2$/g) was determined from the absorbing amount of nitrogen at a liquid nitrogen temperature by the BET method. Further, the pore volume (cc/g) was measured by using a mercury porosimeter. The results obtained are shown in Table 2.

COMPARATIVE EXAMPLE 4

The same procedure as described in Example 3 was repeated except for using the catalyst taken out of the reaction tube, after the reaction had been conducted in the same manner as described in Comparative Example 2 for 3,800 hours. The deposition rate of high boiling point substances, specific surface area and pore volume were measured in the same manner as described in Example 3. The results obtained are shown in Table 2.

TABLE 2

|  | Example 3 | | Comparative Example 4 | |
| --- | --- | --- | --- | --- |
|  | Before Reaction | After Reaction for 8,600 hours | Before Reaction | After Reaction for 3,800 hours |
| Catalyst Pd Concentration (% by weight) | 4.7 | 4.6 | 4.7 | 3.6 |
| Deposition Rate of High Boiling Point Substances (% by weight) | — | 1.6 | — | 32 |
| Specific Surface Area (m$^2$/g) | 170 | 170 | 1058 | 680 |
| Pore Volume (cc/g) | 0.91 | 0.91 | 0.69 | 0.38 |

As is apparent from the results shown above, a catalyst which is useful for acyloxylation and which has a high activity and a very low deactivation rate with the lapse of time can be obtained by using a solid carrier having a specific structure as a carrier for the catalyst comprising palladium and tellurium as active components. Further, by using the catalyst of the present invention, the acyloxylation of a conjugated diene compound can be advantageously performed on an industrial scale.

While the invention has been described in detail and with reference to specific embodiments thereof, it will be apparent to one skilled in the art that various changes and modifications can be made therein without departing from the spirit and scope thereof.

What is claimed is:

1. A process for producing an unsaturated glycol diester which comprises reacting a conjugated diene with a carboxylic acid and molecular oxygen in the presence of a solid catalyst comprising (1) palladium and (2) tellurium as active components supported on a carrier, wherein said carrier is a solid carrier in which a proportion of the volume of pores having a pore radius in the range of from 5 to 50 nm is 80% or more relative to the total volume of pores having a pore radius in the range of from 1.8 to 10,000 nm.

2. A process for producing an unsaturated glycol diester as claimed in claim 1, wherein the amount of tellurium supported on the carrier is from 0.05 to 5 gram atom per gram atom of palladium supported on the carrier.

3. A process for producing an unsaturated glycol diester as claimed in claim 1, wherein the amount of tellurium supported on the carrier is from 0.15 to 4 gram atom per gram atom of palladium supported in the carrier.

4. A process for producing an unsaturated glycol diester as claimed in claim 1, wherein the amount of tellurium supported on the carrier is from 0.15 to 0.5 gram atom per gram atom of palladium supported on the carrier.

5. A process for producing an unsaturated glycol diester as claimed in claim 1, wherein said conjugated diene is selected from the group consisting of butadiene, isoprene and an alkyl-substituted butadiene.

6. A process for producing an unsaturated glycol diester as claimed in claim 1, wherein a proportion of said volume of pores having a pore radius in the range of from 5 to 50 nm is 85% or more relative to the total volume of pores having a pore radius in the range of from 1.8 to 10,000 nm.

7. A process for producing an unsaturated glycol diester as claimed in claim 1, wherein a proportion of said volume of pores having a pore radius in the range of from 5 to 50 nm is 90% or more relative to the total volume of pores having a pore radius in the range of from 1.8 to 10,000 nm.

8. A process for producing an unsaturated glycol diester as claimed in claim 1, wherein said carboxylic acid is an aliphatic carboxylic acid.

9. A process for producing an unsaturated glycol diester as claimed in claim 1, wherein said carboxylic acid is a lower aliphatic monocarboxylic acid.

10. A process for producing an unsaturated glycol diester as claimed in claim 9, wherein said lower aliphatic monocarboxylic acid is acetic acid, propionic acid or butyric acid.

11. A process for producing an unsaturated glycol diester as claimed in claim 1, wherein the reaction is carried out in the presence of a solvent which is inert to the reaction.

12. A process for producing an unsaturated glycol diester as claimed in claim 1, wherein said molecular oxygen is oxygen contained in air.

13. A process for producing an unsaturated glycol diester as claimed in claim 1, wherein said solid catalyst is in a fixed bed system, a fluidized bed system or a suspended bed system.

14. A process for producing an unsaturated glycol diester as claimed in claim 1, wherein the reaction is carried out at a reaction temperature of from 20° to 150° C.

15. A process for producing an unsaturated glycol diester as claimed in claim 1, wherein the reaction is carried out at a reaction temperature of from 50° to 120° C.

16. A process for producing an unsaturated glycol diester as claimed in claim 1, wherein the reaction is carried out at a pressure of from 5 to 100 kg/cm².

17. A process for producing an unsaturated glycol diester as claimed in claim 1, wherein said solid carrier is selected from the group consisting of silica, alumina, titania, zeolite and silica-alumina.

18. A process for producing an unsaturated glycol diester as claimed in claim 1, wherein said solid carrier has a specific surface area of less than 200 m²/g.

* * * * *